US00PP17342P2

(12) United States Plant Patent
Booman

(10) Patent No.: US PP17,342 P2
(45) Date of Patent: Jan. 9, 2007

(54) ***BEGONIA* PLANT NAMED 'LIBRA'**

(50) Latin Name: *Begonia rex hybrid*
Varietal Denomination: Libra

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 11/141,565

(22) Filed: May 31, 2005

(51) Int. Cl.
*A01H 5/00* (2006.01)

(52) U.S. Cl. ..... Plt./343

(58) Field of Classification Search ..... Plt./343
See application file for complete search history.

*Primary Examiner*—Kent Bell
(74) *Attorney, Agent, or Firm*—C. A. Whealy

(57) ABSTRACT

A new and distinct cultivar of *Begonia* plant named 'Libra' characterized by its upright, outwardly spreading and mounded plant habit; vigorous growth habit; does not become dormant during the winter; large rugose leaves with "corkscrew" bases; silvery green-colored leaves with dark green-colored spots and splotches and dark burgundy-colored centers and margins; and burgundy-colored leaf petioles.

1 Drawing Sheet

Botanical designation: *Begonia rex* hybrid.
Cultivar denomination: 'Libra'.

BACKGROUND OF THE INVENTION

The present Invention relates to a new and distinct cultivar of *Begonia*, botanically known as *Begonia rex* hybrid, commercially known as *Rex Begonia,* and hereinafter referred to by the cultivar name 'Libra'.

The new *Rex Begonia* is a product of a planned breeding program conducted by the Inventor in Vista, Calif. The objective of the breeding program is to create new compact vigorous *Rex Begonia* plants with attractive foliage coloration.

The new *Rex Begonia* originated from a chance cross-pollination in February, 2001 of two unknown selections of *Rex Begonia*. The new *Rex Begonia* was discovered and selected as a single plant from within the resulting progeny of the chance cross-pollination in Vista, Calif. in April, 2002.

Asexual reproduction of the new *Begonia* by leaf cuttings in a controlled environment in Vista, Calif. since November, 2002, has shown that the unique features of this new *Begonia* are stable and reproduced true to type in successive generations.

SUMMARY OF THE INVENTION

The new *Begonia* has not been observed under all possible environmental conditions. The phenotype may vary somewhat with variations in environment such as temperature and light intensity without, however, any variance in genotype.

The following traits have been repeatedly observed and are determined to be the unique characteristics of 'Libra'. These characteristics in combination distinguish 'Libra' as a new and distinct cultivar:

1. Upright, outwardly spreading and mounded plant habit.
2. Vigorous growth habit.
3. Does not become dormant during the winter.
4. Large rugose leaves with "corkscrew" bases.

5. Silvery green-colored leaves with dark green-colored spots and splotches and dark burgundy-colored centers and margins.
6. Burgundy-colored leaf petioles.

Plants of the new *Rex Begonia* can be compared to plants of the *Rex Begonia* cultivar Beau Rouge, not patented. In side-by-side comparisons conducted in Vista, Calif., plants of the new *Rex Begonia* differed from plants of the culitvar Beau Rouge in the following characteristics:

1. Plants of the new *Rex Begonia* had smaller leaves than plants of the cultivar Beau Rouge.
2. Leaves of plants of the new *Rex Begonia* had "corkscrew" bases whereas leaves of plants of the cultivar Beau Rouge did not have "corkscrew" bases.
3. Plants of the new *Rex Begonia* had thicker petioles than plants of the cultivar Beau Rouge.
4. Plants of the new *Rex Begonia* and the cultivar Beau Rouge differed in leaf coloration.
5. Plants of the new *Rex Begonia* did not become dormant during the winter whereas plants of the cultivar Beau Rouge became dormant during the winter.

Plants of the new *Rex Begonia* can be compared to plants of the *Rex Begonia* cultivar Mini Merry Christmas, not patented. In side-by-side comparisons conducted in Vista, Calif., plants of the new *Rex Begonia* differed from plants of the cultivar Mini Merry Christmas in the following characteristics:

1. Plants of the new *Rex Begonia* were larger than plants of the cultivar Mini Merry Christmas.
2. Plants of the new *Rex Begonia* had larger leaves and thicker petioles than plants of the cultivar Mini Merry Christmas.
3. Leaves of plants of the new *Rex Begonia* had "corkscrew" bases whereas leaves of plants of the cultivar Mini Merry Christmas did not have "corkscrew" bases.
4. Leaves of plants of the new *Rex Begonia* were not as undulating as leaves of plants of the cultivar Mini Merry Christmas.
5. Plants of the new *Rex Begonia* and the cultivar Mini Merry Christmas differed in petiole coloration.

Plants of the new *Rex Begonia* can also be compared to plants of the *Rex Begonia* cultivar Albuquerque Midnight Sky, disclosed in U.S. Plant Pat. No. 11,977. In side-by-side comparisons conducted in Vista, Calif., plants of the new *Rex Begonia* differed from plants of the cultivar Albuquerque Midnight Sky in the following characteristics:

1. Leaves of plants of the new *Rex Begonia* had "corkscrew" bases whereas leaves of plants of the cultivar Albuquerque Midnight Sky did not have "corkscrew" bases.
2. Plants of the new *Rex Begonia* and the cultivar Albuquerque Midnight Sky differed in leaf coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Rex Begonia.*

The photograph at the top of the sheet is a close-up view of typical leaves of 'Libra'.

The photograph at the bottom of the sheet comprises a side perspective view of a typical plant of 'Libra' grown in a container.

DETAILED BOTANICAL DESCRIPTION

The aforementioned photographs and following observations, measurements and values describe plants grown in a polyethylene-covered greenhouse in Vista, Calif., during the fall and winter under conditions which approximate commercial production practices. After the cuttings were rooted, plants were planted in 15-cm containers and grown for about 14 weeks with day temperatures ranging from 21 to 27° C., night temperatures ranging from 18 to 21° C., and light levels about 1,200 to 1,500 foot-candles. In the following description, color references are made to The Royal Horticultural Society Colour Chart, 1995 Edition, except where general terms of ordinary dictionary significance are used.

Botanical classification: *Begonia rex* hybrid cultivar Libra.

Parentage: Chance cross-pollination of two unknown selections of *Begonia rex* hybrid.

Propagation:

*Type.*—By leaf cuttings.

*Time to initiate roots, summer and winter.*—About four weeks at 21° C.

*Time to develop roots, summer.*—About seven weeks at 21° C.

*Time to develop roots, winter.*—About eight weeks at 21° C.

*Root description.*—Fine; off-white in color.

*Rooting habit.*—Freely branching.

Plant description:

*Plant form.*—Rosette; dwarf; full and dense; uniform; upright and outwardly spreading potted plant; freely basal branching with good leaf petiole strength.

*Growth habit.*—Rapid growth rate; vigorous.

*Branching habit.*—Freely basal branching with about twelve lateral branches per plant.

*Plant height.*—About 14 cm.

*Plant width.*—About 27 to 32 cm.

*Lateral branch description.*—Length: About 5 cm. Diameter: About 9 mm. Internode length: About 6 mm. Strength: Strong. Texture: Pubescent; scattered hairs; succulent. Color: 183A.

*Foliage description.*—Arrangement: Alternate; simple. Length: About 13 cm. Width: About 9.5 cm. Shape: Asymmetrically cordate. Apex: Acute. Base: "Corkscrew". Margin: Serrate; undulate. Texture: Leatherly, rugose; pubescence on veins on both upper and lower surfaces. Venation: Palmate; reticulate. Color: Developing leaves, upper surface: 146A; towards the margin, 59A. Developing leaves, lower surface: 146A overlain with reddish pubescence, 182A. Fully expanded leaves, upper surface: Margin, 187A; outer band interior to margin, 191A with random dots and splotches of 147A; central area, 187B to 187C. Fully expanded leaves, lower surface: Ground color, 148B; towards the margin, 187A; irregular central area, 187B. Venation, upper surface: 191A. Venation, lower surface: 183A.

*Petiole.*—Length: About 8.5 cm. Diameter: About 5 mm. Shape: Longitudinally channeled. Texture, upper and lower surfaces: Pubescent. Color, upper and lower surfaces: 183B.

*Stipules.*—Length: About 1.5 cm. Diameter: About 1 cm. Shape: Deltoid. Color, upper and lower surfaces: 183B.

Flower description: Flower development has not been observed.

Disease/pest resistance: Plants of the new *Rex Begonia* have not been noted to be resistant to pathogens and pests common to *Rex Begonias.*

Temperature tolerance: Plants of the new *Rex Begonia* tolerate temperatures ranging from 0 to 35° C.

It is claimed:

1. A new and distinct *Begonia* plant named 'Libra' as illustrated and described.

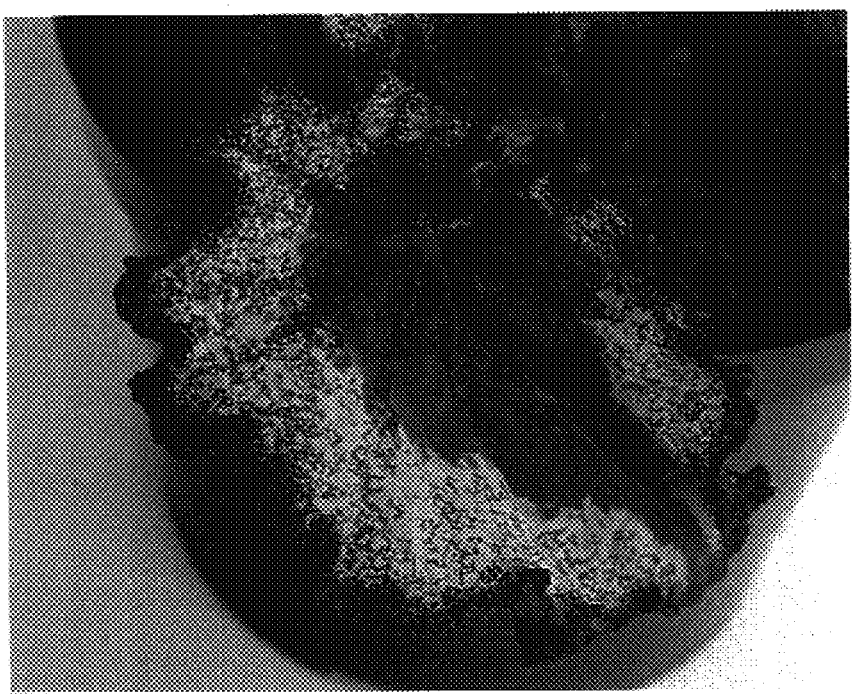
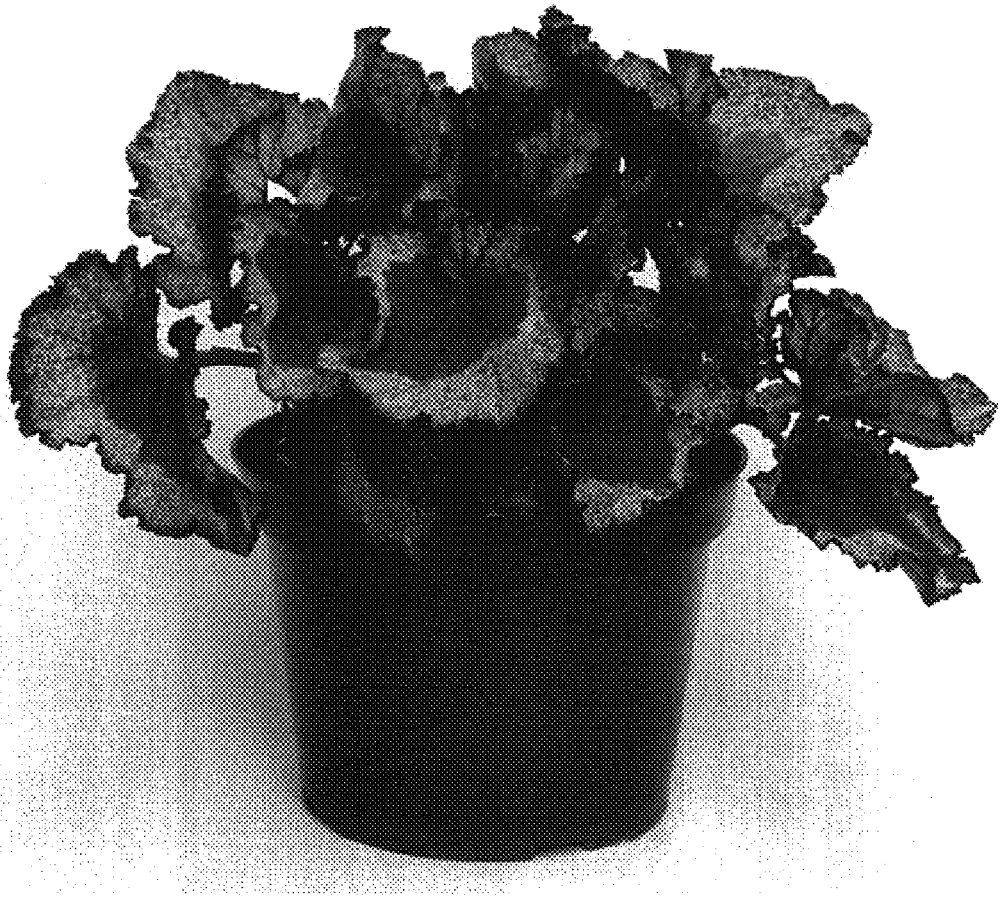

* * * * *